United States Patent [19]

Neipel et al.

[11] Patent Number: 5,814,475

[45] Date of Patent: Sep. 29, 1998

[54] HUMAN HERPESVIRUS TYPE 6 PROTEIN P100, THE CORRESPONDING DNA SEQENCES, THEIR PREPARATION AND USE

[75] Inventors: Frank Neipel, Erlangen; Bernhard Fleckenstein, Wiesenthau, both of Germany

[73] Assignee: Behring Diagnostics GmbH, Marburg, Germany

[21] Appl. No.: 266,311

[22] Filed: Jun. 27, 1994

Related U.S. Application Data

[63] Continuation of Ser. No. 126,435, Sep. 24, 1993, abandoned, which is a continuation of Ser. No. 908,041, Jul. 6, 1992, abandoned.

[30] Foreign Application Priority Data

Jul. 8, 1991 [EP] European Pat. Off. ............... 91111338

[51] Int. Cl.[6] .......................... C07H 21/04; C12N 15/09; C12N 15/38; C12P 21/00
[52] U.S. Cl. ....................... 435/69.1; 435/69.1; 435/70.1; 435/70.3; 435/71.1; 435/71.2; 435/172.3; 435/243; 435/254.2; 435/254.21; 435/320.1; 435/325; 435/410; 435/822; 435/849; 435/942; 536/23.42; 935/23; 935/24; 935/52; 935/66
[58] Field of Search .................................. 435/69.1, 69.3, 435/69.7, 70.1, 70.3, 71.2, 172.3, 240.2, 240.21, 320.1, 71.1, 243, 254.2, 254.21, 325, 410, 822, 849, 942; 536/23.1, 23.4, 23.7, 23.72; 935/23, 24, 52, 66

[56] References Cited

FOREIGN PATENT DOCUMENTS 4013536 11/1990 Germany .
WO 91/02794 3/1991 WIPO .

OTHER PUBLICATIONS

Josephs et al., "Genomic Analysis Of The Human B–Lymphotropic Virus (HBLV)," Science, vol. 234, pp. 601–603 (Oct. 31, 1986).

Neipel et al., "Gene For The Major Antigenic Structural Protein (p100) Of Human Herpesvirus 6," The Journal Of Virology, vol. 66, No. 6, pp. 3918–3924 (Jun. 1992).

Identification, Cloning, and Expression of the Major Capsid Protein Gene of Human Herpesvirus 6, E. Littler et al., Journal of Virology, vol. 64, No. 2 Feb. 1990, pp. 714–722.

Serological Crossreaction of Human Herpesvirus 6 with Cytomegalovirus, C. Larcher et al., The Lancet, Oct. 22, 1988, pp. 963–964.

The Unique Region of the Human Herpesvirus 6 Genome is Essentially Collinear With the UL Segment of Human Cytomegalovirus, F. Neipel et al., Journal of General Virology (1991), 72, pp. 2293–2297.

Identification of a Nucleocapsid Protein as a Specific Serological Marker of Human Herpesvirus 6 Infection, M. Yamamoto et al., Journal of Clinical Microbiology, vol. 28, No. 9, Sep. 199, pp. 1957–1962.

Identification, Characterization, and Sequence Analysis of a cDNA Encoding a Phosphoprotein of Human Herpesvirus 6, C.K. Chang et al., Journal of Virology, vol. 65, No. 6, Jun. 1991, pp. 2884–2894.

Human Herpesvirus 6 Is Closely Related to Human Cytomegalovirus, G.L. Lawrence et al., Journal of Virology, vol. 64, No. 1, Jan. 1990, pp. 287–299.

*Primary Examiner*—Brian R. Stanton
*Attorney, Agent, or Firm*—Finnegan, Henderson, Farabow, Garrett & Dunner, L.L.P.

[57] ABSTRACT

The invention relates to the human herpesvirus type 6 protein p100 and parts thereof having its specific immunological properties. It further relates to antibodies directed to them and to the corresponding DNA sequences. They can be used in pharmaceutical or diagnostic compositions, optionally together with other HHV-6 proteins or the corresponding DNA sequences.

12 Claims, 11 Drawing Sheets

SEQUENCES OF THE VIRAL INSERTS OF CLONES pMF94 AND pMF295. BOTH SEQUENCES ARE PART OF THE MAJOR CAPSID PROTEIN GENE OF HHV-6 AS PUBLISHED IN (LITTLER ET AL. 1990).

NUCLEOTIDE SEQUENCE OF pMF94

```
  1 GAATTCCTGA CGCCAGCGCC ACAGGCCTTG TTATTTGATA GTGCCGGGAG
 51 TACGCAGAAG TAAAATATCT TGCTCAGGAT GGTGGTTTCG TTCGATGGTC
101 TGTCATTGTC GGTAAAGACG ACGCTTGAAT CTATTAGATT CATTCTTTGC
151 ACATCGGATA TTTCGTAATT TCTAACTCTT ACGGTGTTCT GTGTCAGTGG
201 TGTATCATCC GCTGTTATTT TTGCATTCGT GTCGTTTCTG GGCATGGTAT
251 GGACGAACGG GCAGAACAGA CGTCCGTCGA ACAACGCGTT GGCGAAATTC
301 ACCAGAGGTT CGCCGCAAAG TTGCTCGTTG AGGTTGGAGA TAGAGATTGT
351 TCTCTTCACT AGGCGAATTA GCGACACAAG ATTTCTGTAG TGAGCGAAAG
401 CTGCTCCCGG GATCAGTTCG TCGCCCATGT GGTTGGAATT C (SEQ ID NO: 5)
```

NUCLEOTIDE SEQUENCE OF pMF295

```
  1 CCGTGTGAAA TTAAACGACA CCATGGAAAA CAACCTACCC ACCAGCGTTT
 51 TTTTCCACAA TAAAGACCAA GTCGTGCAGC GAATTGATTT TGCCGACATA
101 TTACCGTCGG TTTGCCATCC CATTGTCCAC GACTCGACCA TCGTCGAACG
151 ACTCATGAAA AGCGAACCAT TGCCTACCGG CCACCGCTTT TCCCAACTAT
201 GTCAACTAAA AATTACCCG (SEQ ID NO:6)
```

FIG. 1

SEQUENCE OF THE VIRAL INSERT OF CLONE pMF90. THE
SEQUENCE IS IDENTICAL WITH NUCLEOTIDES 117-194 OF THE
SEQUENCE PUBLISHED IN (CHANG AND BALACHANDRAN, 1991).

```
  1       CCA CTTTTTGAAA GTTTTATGAA CATCATCTCG AATCCTGAGG
 51   TTACGAAGAT GTACATTCAG CATGATAGTG ATCTGTATAC GAGGGTTTTG
101   GTAACGGCTT CCGATACATG TACACAGGCG TCGGTTCCCT GTGTGCACGG
151   ACAAGAAGTG GTGCGAGACA CCGGGAGATC GCCGTTGAGG ATTGACCTTG
201   ATCATTCGAC CG (SEQ ID NO:7)
```

FIG. 2

COMPLETE SEQUENCE OF THE HHV-6 EcoRI FRAGMENTS NUMBERED
6 AND 7 (STARTING FROM THE LEFT END). THESE FRAGMENTS
CONTAIN THE ENTIRE p100 GENE OF HHV-6. THE POSITION
OF pROS EXPRESSION CLONES IS INDICATED WITHIN THE
SEQUENCE.

```
    E
    c
    o
    R
    I
    GAATTCCTATGTTNCGCCCCGTGCTAGATGTTTTACTTTCAGTCTTTTTACGCCGGTGTAAGGTTTTGTACC
1------------------------------------------------------------------------72
    TGATAGTTGCGATTATAGCTAGCATGCTTATACTATATGAACAGACTGCATGATAGATGAAGTAAACTAACT
73-----------------------------------------------------------------------144
    GACAGAAAAAACGGTTGAATGAGAACAGTTGCTTTCTGTTCACTGTCATAAAAAAGACACACCACATGAGCA
145----------------------------------------------------------------------216
    CAAAATCGCTAGCAAAGAGTGTGATGACGTAAAATGAAGTAGCGTTATGTTTTGCGACTCTGTGGTAGAGAA
217----------------------------------------------------------------------288
    TCATGGTGGTAACCACTATAATGATCATGGGGATAGATGTGGTGAGCGTGATTCCGGTAACTGCGCTCTCCA
289----------------------------------------------------------------------360
    TGATTCGTGCTGTCTTTAGCGTGGGTGTCGAGGTACAGGAAGCATTGCCTTTGAACTCTTCATTGCGCTATT
361----------------------------------------------------------------------432
    AAAGATATTGAATGTTATTTTCATGTTACGCTACATTAAAATATTCGGTAACAATGATGTCTGAAGACTTAC
433----------------------------------------------------------------------504
    CAGAAGTTTGGACAGCTCAATGACAGTGTCCATCTCGTCGCTTGTCAGTTTTCTGTGTGGGTAAAAAAAAGA
505----------------------------------------------------------------------576
    CTATTAAACATTGAATGTTGGCGGAAATGAGCAGTTCTGTTTTTGAGTTTGTTTTCTAAAATATGGATCTGC
577----------------------------------------------------------------------648
                                                                  M  D  L  Q-
    AAAGACATCCGATTCCGTTTGCGTGGCTAGATCGAGACAAAGTTGAGCGTCTTACAGATTTTCTCAGCAATT
649----------------------------------------------------------------------720
     R  H  P  I  P  F  A  W  L  D  R  D  K  V  E  R  L  T  D  F  L  S  N  L-
    TGGAAAGACTGGATAATGTAGATTTGCGAGAGcaTCCCCATGTGACTAATTCTTGTGTCGTGAGAGAGGGAG
```

FIG. 3-1

```
722------------------------------------------------------------------------792
     E   R   L   D   N   V   D   L   R   E   H   P   H   V   T   N   S   C   V   V   R   E   G   D-
                             D
                             r  ----BEGIN OF pDF446-4
                             a
                             I
    ACGATGTAGACGATTTAAAAACATTGTATAACCTACTAGTGTTATGGCTTATGTATCACTACGTCTTATCTA
793------------------------------------------------------------------------864
     D   V   D   D   L   K   T   L   Y   N   L   L   V   L   W   L   M   Y   H   Y   V   L   S   K-
    AAAGGAAGCCGGATTATAATGCTATATGGCAAGACATCACGAAACTCCAAAGTGTCGTAAACGAGTACTTAA
865------------------------------------------------------------------------936
     R   K   P   D   Y   N   A   I   W   Q   D   I   T   K   L   Q   S   V   V   N   E   Y   L   N-
    ACTCCAAGGTCTGAATAAAGGAATTTTTGAAAAATATGTTCACGAACAAAGAAAAGTTTGAATCGCAATTCA
937-----------------------------------------------------------------------1008
     S   K   G   L   N   K   G   I   F   E   N   M   F   T   N   K   E   K   F   E   S   Q   F   S-
    GTGATATTAATCGCGCTTTACTGCGTTTAGGAAACTTTATTAAGTGGGGTAGCAATGTTGCGATCGATACTC
1009----------------------------------------------------------------------1080
     D   I   N   R   A   L   L   R   L   G   N   F   I   K   W   G   S   N   V   A   I   D   T   P-
    CTTATGTAAATCTTACTGCAGAAGACAGCAGCGAGATAGAAAATAATTTGCAAGATGCTGAAAAAAACATGC
1081----------------------------------------------------------------------1152
     Y   V   N   L   T   A   E   D   S   S   E   I   E   N   N   L   Q   D   A   E   K   N   M   L-
    TGTGGTATACCGTCTATAACATAAATGACCCCTGGGACGAAAACGGTTACTTAATAACGAGTATTAATAAAT
1153----------------------------------------------------------------------1224
     W   Y   T   V   Y   N   I   N   D   P   W   D   E   N   G   Y   L   I   T   S   I   N   K   L-
    TAATTTATCTCGGTAAGTTATTTTTAGCGTTAACTCAGTCCTGGTCAAAGCTAGAAAAGGTTGCTATGAGTC
1225----------------------------------------------------------------------1296
     I   Y   L   G   K   L   F   L   A   L   T   Q   S   W   S   K   L   E   K   V   A   M   S   Q-
    AAATTGTAATCACGCAAAATCATCTCTCGGGTCATTTGAGGAGGCACGACAATTTTAATATTGTATATTCTC
1297----------------------------------------------------------------------1363
     I   V   I   T   Q   N   H   L   S   G   H   L   R   R   H   D   N   F   N   I   V   Y   S   H-
    ATAGGGTTTTGCAGACTCCTCTGACTGGTCAAAGAGTAGAGAGTTTTCTGAAAATAATCACCAGTGATTATG
1369----------------------------------------------------------------------1440
     R   V   L   Q   T   P   L   T   G   Q   R   V   E   S   F   L   K   I   I   T   S   D   Y   D-
                                                                           H
                                                                           a
                                          END OF pDF446-4----- e -BEGIN
                                                                           I  OF
                                                                           I  pD2Hae
                                                                           I
    ATATTATCAAAAGTAGTCTGGAATCACACAGCGCGTCGAAAGCATTTTCGATGTCTGAGATTGGGCCTAATT
1441----------------------------------------------------------------------1512
```

FIG. 3-2

```
      I   K S S L E S H S A S K A F S M S E I G P N S-
CTTT?A?GGATTTCGTCCCTTTACGCGGCGATATACATTCAAATTTGACTTTACCTAGTATGTCTATAGATA
1513----------------------------------------------------------------1584
    L ? D F V P L R G D I H S N L T L P S M S I D T-
CAAAG?AATCATCTTTAGATCCGGCTCGTCTGAAAAAAAGTAATTCCAGAAGTTTGGATAGTTTCTTAAGAA
1585----------------------------------------------------------------1656
    K ? S S L D P A R L K K S N S R S L D S F L R M-
TGCAGAGACAACCTAAATTTCTAGAGTTGGATAGCGTTGATAATGCCGGGGAAAAAATTTTACTAAAGGAAG
1657----------------------------------------------------------------1728
    Q R Q P K F L E L D S V D N A G E K I L L K E A-
CAACACTCGGGGGTGAAAACGTTAAAGCGACAACGCCTGCTTCCTCTGTCTCTTTAATGTCCGGAGTTGAGT
1729----------------------------------------------------------------1800
    T L G G E N V K A T T P A S S V S L M S G V E S-
CGCCGTCGTCTTTCACTTCTACCAATCTGGATCTGCCGTTGTCGTCTTTCACTTCTACTAATCTGGATCTGC
1801----------------------------------------------------------------1872
    P S S F T S T N L D L P L S S F T S T N L D L R-
                          H
                          a
     END OF pD2Hae ----- e ------ BEGIN OF pDF446-3
                          I
                          I
                          I
GAGATAAGTCGCACGGTAATTATAAAATTGGCCCTTCGGGGATTTTAGATTTTAATGTTAAATTTCCACCTA
1873----------------------------------------------------------------1944
    D K S H G N Y K I G P S G I L D F N V K F P P N-
ATGCGCAATTGAATACGAACGGTGTGGATTTACTACAGGATAAAACTTCGATCGGGAGTCCCAGTAGCGGTA
1945----------------------------------------------------------------2016
    A Q L N T N G V D L L Q D K T S I G S P S S G I-
TTACCGATGTGGTAAATGGTTTCGCTAATCTCAATCTGCATCAGAATAAATCAAATGTTTCGCCACCGTGGA
2017----------------------------------------------------------------2088
    T D V V N G F A N L N L H Q N K S N V S P P W S-
GCAGAAACACAGCGGCGAATGCGGACTTTTTAGATCCGGTGCATCGCTTTGTTCCTGAGCAGACAGGGACAC
2089----------------------------------------------------------------2160
    R N T A A N A D F L D P V H R F V P E Q T G T P-
CCTTCGTGTTGAATAATTCCGACGTGGCGGGATCAGAAGCGAAGCATACGACTTACAGTACGGAGACCGGCG
2161----------------------------------------------------------------2232
    F V L N N S D V A G S E A K H T T Y S T E T G V-
TTTCACCCCGTAACGTTTTTCTCATTAAAGATTTGAGAGGCAAAGACGGTTTTAGGAAACAGAAGCAGTCAG
2233----------------------------------------------------------------2304
    S P R N V F L I K D L R G K D G F R K Q K Q S D-
ATATTCCGAAAAGCTTAACTAAGGAAAGAAATGATAAAGCTATAATGCACTCACGCGAGGTGACCGGAGATT
2305----------------------------------------------------------------2376
```

FIG. 3-3

```
        I  P  K  S  L  T  K  E  R  N  D  K  A  I  M  H  S  R  E  V  T  G  D  S-
                                        E
         END OF pDF446-3 ----  c  ---- BEGIN OF pD2Hind
                                        o
                                        R
                                        I
      CTGGCGATGCGACTGAAACTGTGGGTGCTCGGAATTCCCCGGCGTTGAGAAAAATTAAGCAAGCAAATGATT
2377-----------------------------------------------------------------------2448
         G  D  A  T  E  T  V  G  A  R  N  S  P  A  L  R  K  I  K  Q  A  N  D  F-
      TTTTTGCCGGGTTAAATAAGAAAAATGATCGTGACGTATTAAGAGGGGGGAAAGGAAATAGCAAGGACTTGC
2449-----------------------------------------------------------------------2520
         F  A  G  L  N  K  K  N  D  R  D  V  L  R  G  G  K  G  N  S  K  D  L  H-
      ATTCTGGCGGCAATGCAAAAAAAAAGAAATGTCGGGAAAGTTTAATGACGATAAAGAAATGACGCGAAACG
2521-----------------------------------------------------------------------2592
         S  G  G  N  A  K  K  K  E  M  S  G  K  F  N  D  D  K  E  M  T  R  N  G-
      GACAAGAGCCATCACGTAGTTTAATGGGAGATGCTAGAAATGCCGGAGATGAACAATATATTCAAGCGGGTC
2593-----------------------------------------------------------------------2664
         Q  E  P  S  R  S  L  M  G  D  A  R  N  A  G  D  E  Q  Y  I  Q  A  G  L-
      TCGGGCAGCGAGTTAACAATCTTCTAAGTCAATTTACAAATCTGATTAGTTTAGGCGAGAAGGGCATCGAAG
2665-----------------------------------------------------------------------2736
         G  Q  R  V  N  N  L  L  S  Q  F  T  N  L  I  S  L  G  E  K  G  I  E  D-
      ACATTTTGCAGAATCAGCGCGGGACCGAGTTAAAGTTGGCTACAGAAAACAAGTCGGGACGCGAATCGGAGG
2737-----------------------------------------------------------------------2808
         I  L  Q  N  Q  R  G  T  E  L  K  L  A  T  E  N  K  S  G  R  E  S  E  E-
      AAGCTAACGTAGAAAAAATTCTTGAAGTTAGTAATCCTCAAGATATGTTTAAAAATTTTAGGTTGCAAAACG
2809-----------------------------------------------------------------------2880
         A  N  V  E  K  I  L  E  V  S  N  P  Q  D  M  F  K  N  F  R  L  Q  N  D-
      ATCTCGATTCCGTTCAGTCTCCGTTTAGGCTACCGGATGCTGATTTGTCTCGCGAGTTAGATTCCGCGTCAT
2881-----------------------------------------------------------------------2952
         L  D  S  V  Q  S  P  F  R  L  P  D  A  D  L  S  R  E  L  D  S  A  S  F-
                        H
  END OF pD2Hind -----  i
                        n
              BEGIN     d
             OF pMF101R I
                        I
                        I
      TTAAGGACGCGTTAGACTTGAAGCTTCCGGGTAACGGAGAACGAGAAATAGATCTCGCTCTTGAAAAGTGA
2953-----------------------------------------------------------------------3024
         K  D  A  L  D  L  K  L  P  G  N  G  E  R  E  I  D  L  A  L  E  K  V  K-
```

FIG. 3-4

```
AGGTAGGCGAGACGGAAACCTCAGATTTAAAAGTCGGTCAGGATGAAAGTTTTGTTCCTGCGCAATTAATGA
3025------------------------------------------------------------------3096
      V  G  E  T  E  T  S  D  L  K  V  G  Q  D  E  S  F  V  P  A  Q  L  M  K-
                       END OF pMF101R ──────┐
                                             │
AGGTTGAGACACCTGAAGAAAAAGATGATATAATTGAACAGATGGTTCTGAGGATACGTCAAGACGGGGAAA
3097------------------------------------------------------------------3168
      V  E  T  P  E  E  K  D  D  I  I  E  Q  M  V  L  R  I  R  Q  D  G  E  T-
CTGATGAAAACACCGTCTCTGGGCCGGGAGTCGCTGAGTCTTTGGATATAGAAGCCAAAGGCGAGTCAGCGA
3169------------------------------------------------------------------3240
      D  E  N  T  V  S  G  P  G  V  A  E  S  L  D  I  E  A  K  G  E  S  A  I-
TCGCGTCGTGATGTAAAAAATTTTCTCTGGGGAGTTTCAGGTTGCCAATAAAATGCCCATTCTCAGACAGCT
3241------------------------------------------------------------------3312
      A  S  *
TTGCGATTACGTCTTTTTGTTCATTGTTCTGGCTTGTCATTCTTTCTACATAAAACAGGGTCGCGATAGGTG
3313------------------------------------------------------------------3384
TGCTTTGAGGCAGGATCAGATTTGGAGAAAATGAACGCAGCGTAATGTGCAAAGGTGTTCCCGGGGCCCACA
3385------------------------------------------------------------------3456
GCATCACCTGGGTTTCGAAGAATCCTTCGTTCTGGTAGCCGGATATGAGGATTTGCTTGTCGGGCTTTGTGA
3457------------------------------------------------------------------3528
AATATCGGATAGGTAGAATTACTATGTGGCATCGGCTTGGATAGAAATGGATGTCATATGGTGCGTGTACAA
3529------------------------------------------------------------------3600
GTAGCTCGTAATAATTTGGGTTGTGTTGCAGTTGTATCGTTGCGTTTAGTACGTCTCCTGTAAAATATAATT
3601------------------------------------------------------------------3672
TCGGGTTACTGGAAAATAACAGNGGTTCGGGCTCTTCGATTTGCGTTACCACTTCAAACTGAACTATTAAAT
3673------------------------------------------------------------------3744
ATTTCGGTAGATTTTCCGTTGTTAGTAAAGAAGGGATTTGCTCGCAGCATACAGTGGCTAGTGTTCCAAAAA
3745------------------------------------------------------------------3816
                                                                   E
                                                                   c
                                                                   o
                                                                   R
                                                                   I
CTTTTTCTTTGTTTTTGACGAGACCGAGATTTTCAATGTTAATCGAGAATTC (SEQ. ID NO:8)
3817---------------------------------------------3868
```

FIG. 3-5

HUMAN HERPESVIRUS TYPE 6 PROTEIN P100, THE CORRESPONDING DNA SEQENCES, THEIR PREPARATION AND USE

This application is a continuation of application Ser. No. 08/126,435 filed Sep. 24, 1993, now abandoned, which is a continuation of application Ser. No. 07/908,041 filed Jul. 6, 1992, now abandoned.

The present invention relates to the human herpesvirus type 6 protein p100 and parts thereof having its specific immunological properties. It further relates to antibodies specifically reacting with the protein or parts thereof and to DNA sequences encoding said protein or parts thereof, to recombinant vectors containing these DNA sequences and to host organisms transformed with these vectors. Furthermore, it relates to the preparation of the proteins and DNA sequences and their use in pharmaceutical or diagnostic compositions.

BACKGROUND OF THE INVENTION

The human herpesvirus type 6 (HHV-6) has recently been shown to be closely related to human cytomegalovirus (HCMV) on the basis of amino acid sequence homology (Littler et al., 1990; Lawrence et al., 1990; Chang and Balachandran, 1991; Neipel et al., 1991), genomic position and orientation of conserved herpesvirus genes (Neipel et al., 1991), and antigenic properties (Larcher et al., 1988; Yamasoto et al., 1990; Littler et al., 1990). Until today, only two proteins of HhV-6 and their genes have been described in more detail: the major capsid protein (MCP) (Littler et al., 1990) with a molecular weight of 135 kda, and a phosphoprotein of 41 kda termed HHV-6 p41 (Chang and Balachandran, 1991). The latter one is homologous to UL44 of HCMV.

In order to be able to distinguish infections caused by HHV6 and HCMV it is desirable to have a reagent which is specific for the human herpesvirus type 6.

SUMMARY OF THE INVENTION

Thus, the technical problem underlying the present invention essentially is to provide a protein having immunogenic properties and the capability to induce the formation of antibodies lacking crossreactivity with HCMV and other human herpesviruses. Furthermore, it is a technical problem to provide the corresponding DNA sequences.

The solution to this technical problem is achieved by providing the embodiments characterized in the claims.

The present invention therefore relates to a DNA sequence encoding the HHV-6 (human herpesvirus type 6) protein p100 having the amino acid sequence given in FIG. 3 (SEQ ID NO:2) starting from the position corresponding to nucleotide 639 to the position corresponding to nucleotide 3248.

The protein p100 is a structural protein from human herpesvirus type 6 with a molecular weight of about 100 kda that is in part homologous to pp150 of HCMV. It can be obtained by expression of the gene which is located in the region of the EcoRI fragments 6/7 of HHV-6 strain U1102 (distance to the left end of the HHV-6 genome 21–25 kb). The protein p100 has immunogenic properties and lacks crossreactivity with human cytomegalovirus and other human herpesviruses (Yamamoto et al., 1990). It can, therefore, be used as a reagent for detecting HHV-6 antibodies and for the differential diagnosis of HHV-6 infection versus CMV-infection.

The present invention further relates to the corresponding DNA sequence given in FIG. 3 (SEQ ID NO:2) from position 639 to position 3248.

A DNA sequence encoding p100 can be isolated from an HHV-6 genome as disclosed herein. If the obtained DNA sequence differs from the DNA sequence given in FIG. 3, the above DNA can be derived therefrom by conventional in vitro mutagenesis techniques. Furthermore, the person skilled in the art equipped with the technical teaching disclosed herein will be able to obtain the DNA sequences of the present invention by conventional DNA synthesis techniques.

In a further embodiment, the present invention relates to a DNA sequence hybridizing to the above DNA sequence and encoding a protein having the specific immunological properties of the HHV-6 protein p100. In this context, the term "hybridization" refers to conventional hybridization conditions, preferably to hybridization conditions between $T_m \approx -20°$ to $T_m \approx -27°$ C. Most preferably, the term "hybridization" refers to stringent hybridization conditions. The term "having the specific immunological properties" characterizes the entire protein defined by the amino acid sequence in FIG. 3 as well as parts of this protein which react with antibodies specific for the protein and substantially without crossreactivity to components of human cytomegalovirus and other herpesviruses. Examples of such immunogenic parts or epitopes of the protein are the amino acid sequences encoded by the nucleotide sequence given in FIG. 3 from position 2960 to position 3141 (SEQ ID NO:3) or the nucleotide sequence given in FIG. 3 from position 2408 to position 2959. (SEQ ID NO:4) These epitopes may also be used in the diagnostic composition described below.

The present invention further relates to recombinant vectors containing the above DNA sequences whereby the DNA sequences may be under the control of a homologous or heterologous promoter allowing its expression in a desired host cell.

A further embodiment of the present invention is a host organism transformed with one of the recombinant vectors of the present invention wherein the host organism is a bacterium, preferably of the genus Escherichia, a yeast, preferably of the genus Saccharomyces, a plant cell or an animal cell, preferably a mammalian cell.

The present invention also relates to the preparation of the HHV-6 protein p100 which comprises the steps of cultivating a transformed host organism and recovering said protein from the culture.

A further object of the present invention is to provide antibodies specifically reacting with the HHV-6 protein p100 or parts thereof having its specific immunological properties but not with components of human cytomegalovirus and other herpesviruses. The person skilled in the art provided with the proteins and fragments thereof of the present invention can produce these antibodies according to conventional methods. In a preferred embodiment of the antibodies of the present invention, the antibodies are monoclonal antibodies.

Another object of the invention is to provide pharmaceutical compositions containing the HHV-6 protein p100 or parts thereof having its specific immunological properties and/or antibodies directed to them, wherein the pharmaceutical compositions are suitable for the prophylaxis or treatment of HHV-6 infections.

A further object of the invention is to provide a composition containing the HHV-6 protein p100 or parts thereof having its specific immunological properties or the corresponding DNA sequences or antibodies of the invention.

These compositions may additionally contain parts of the major capsid protein gene of HHV-6, especially the DNA sequences given in FIG. 1 (SEQ ID NOS:5 and 6) and/or the polypeptide being encoded by these DNA sequences or parts of the gene encoding the phosphorylated HHV-6 protein of 41 kda, especially the DNA sequence given in FIG. 2 (SEQ ID NO:7) and/or the polypeptide being encoded by these DNA sequences. Since the HHV-6 protein p100 has the capability to induce the formation of antibodies lacking crossreactivity with human cytomegalovirus or human herpesviruses, it may be used in the differential diagnosis for distinguishing whether an infection is caused by HHV-6 or human cytomegalovirus or other herpesviruses.

BRIEF DESCRIPTION OF THE DRAWINGS

The present invention is explained in more detail in the following description and the figures:

FIG. 1 shows the DNA sequences of the viral inserts of clones pMF94 (SEQ ID NO:5) and pMF295 (SEQ ID NO:6). Both sequences are part of the major capsid protein gene of HHV-6 as published in Littler et al., 1990.

FIG. 2 shows the DNA sequence of the viral insert of clone pMF90. (SEQ ID NO:7) The sequence is identical with nucleotides 117–194 of the sequence published in Chang and Balachandran, 1991.

FIG. 3 shows the complete DNA sequence of the HHV-6 EcoRI fragments numbered 6 and 7 (starting from the left end) (SEQ ID NO:8). These fragments contain the entire p100 gene of HHV-6. Furthermore, the amino acid sequence of p100 is shown.

DESCRIPTION OF THE PREFERRED EMBODIMENTS

The DNA sequences encoding the immunogenic proteins and parts thereof were identified in a genomic HHV-6 gene bank with mono- and polyspecific rabbit antisera against HHV-6 proteins.

Figure 4:
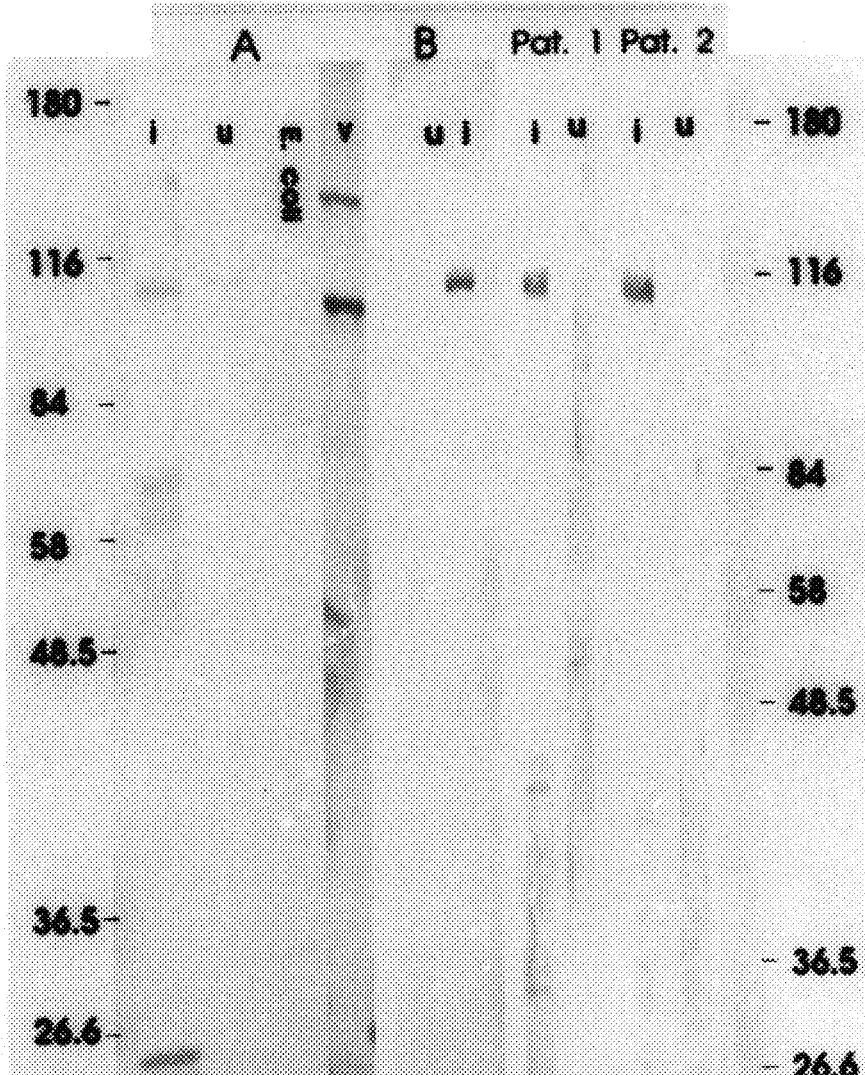
FIG. 4 shows a Western blot analysis wherein antiserum of rabbits immunized with HHV-6 infected HSB-2 cells and antibodies against the HHV-6 protein p100 purified from this antiserum are reacted with viral proteins.

Rabbits were immunized with whole HHV-6 infected HSB-2 cells. The obtained antiserum reacted with at least 7 viral proteins (FIG. 4). Antibodies against a 100 kda protein of HHV-6 were purified from this serum. For this purpose, entire viral protein was subjected to preparative SDS polyacrylamide electrophoresis. Viral protein with a molecular weight of 100 kda was transferred to nitrocellulose membranes and incubated with the diluted rabbit serum. Antibodies that were specifically bound on the nitrocellulose sheets were eluted with 100 mM glycin at pH 2.7. The obtained anti-bodies reacted specifically with an HHV-6 virion protein of about 100 kda (FIG. 4). Both serum preparations were used to screen the genomic library.

Figure 5:
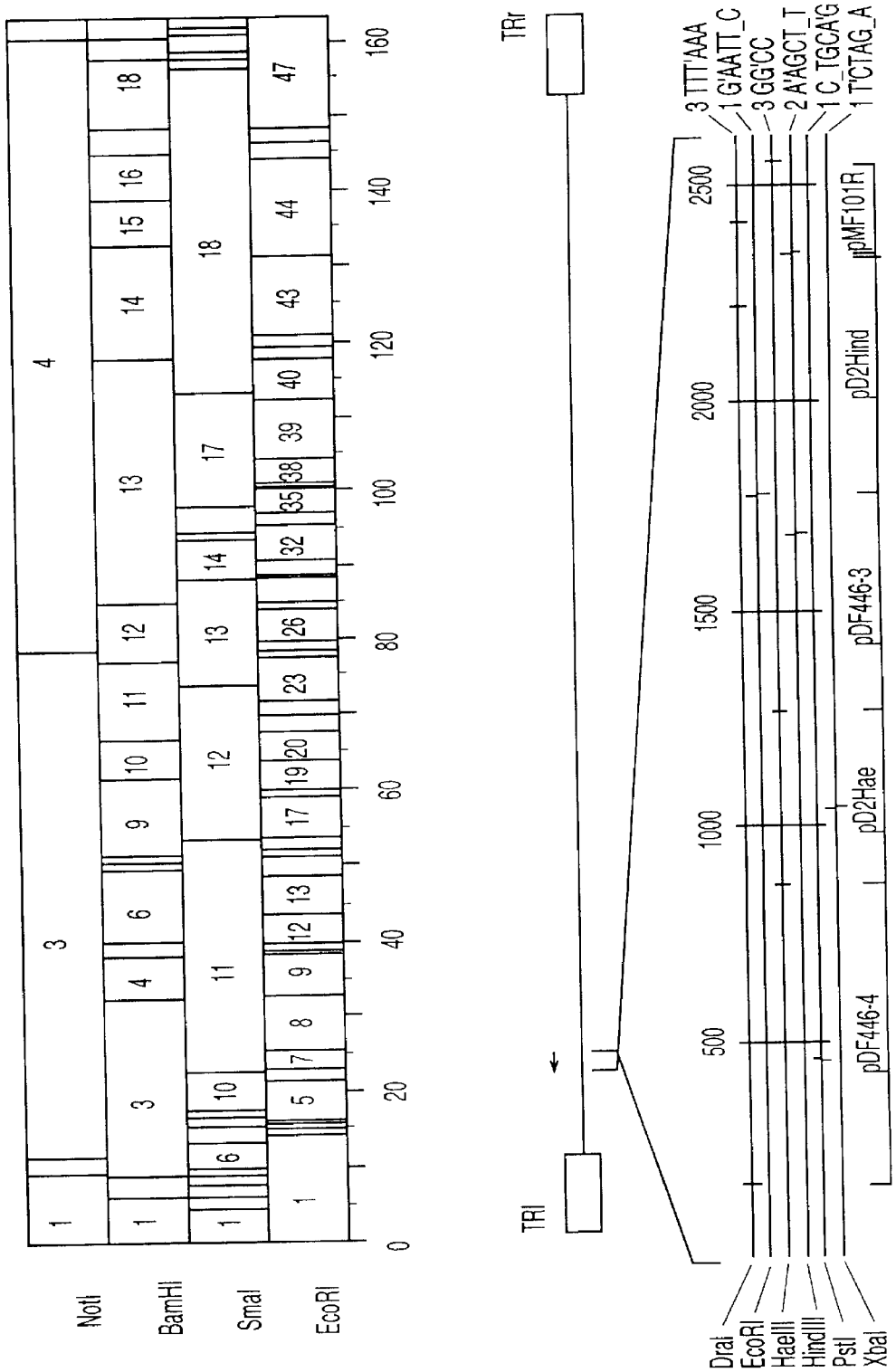
FIG. 5 shows the restriction map of the HHV-6 genome.

The construct of a genomic library DNA from cosmids containing the entire HHV-6 genome in overlapping fragments was sheared by sonication. After addition of EcoRI linkers, EcoRI digestions and size fractionation it was ligated into the commercially available vector lambda zapII (Stratagene Inc., La Jolla, U.S.A.). After in vitro packaging a gene bank of $3 \times 10^5$ independent recombinants was obtained. Positive clones were identified by immunological screening using the sera mentioned and a commercially available detection system ('Pica blue', Stratagene Inc., La Jolla, U.S.A.). The identified lambda clones were then subcloned into the Bluescript SK- vector by 'in vivo excision' following the supplier's instructions (Stratagene Inc.). Four clones that were especially reactive in Western blots (pMF101, pMF90, (SEQ ID NO:7) pMF94, (SEQ ID NO:5) pMF295) (SEQ ID NO:5) were chosen for further characterization. The inserts of these clones were sequenced by Sanger's chain termination method. Data were analyzed by the Genetics Computer Group (GCG, Madison, Wis. U.S.A.) sequence analysis package. The predicted amino acid sequences were used for homology searches with the computer program FASTA (Pearson & Lipman, 1988) in a library containing all of the published herpesvirus sequences. The clones pMF94 (SEQ ID NO:6) and pMF295 (SEQ ID NO:6) were found to contain parts of the published Major Capsid Protein gene of HHV-6 (FIG. 1) (Littler et al., 1990), while pMF90 (SEQ ID NO:7) contains part of an open reading frame homologous to UL44 of HCMV (FIG. 2). The corresponding HHV-6 gene has recently been identified using monoclonal antibodies against a phosphorylated HHV-6 protein of 41 kda (Chang and Balachandran, 1991). However, the epitope identified by Chang et al. is located after amino acid 227 of their sequence, while pMF90 (SEQ ID NO:7) covers amino acids 119–187 only. No homologous gene could be found for the predicted amino acid sequence of clone pMF101. The insert of pMF101 was used to locate the gene within the virus genome. By hybridization with 7 cosmid clones that encompass the entire HHV-6 genome (Neipel et al., 1991) it could be located within an 1.4 kb EcoRI fragment close to the left terminal repeat (FIG. 5). Further sequencing in this area revealed an open reading frame coding for a protein of 870 amino acids with a predicted molecular weight of 97 kda (termed p100 hereinafter).

Figure 6:
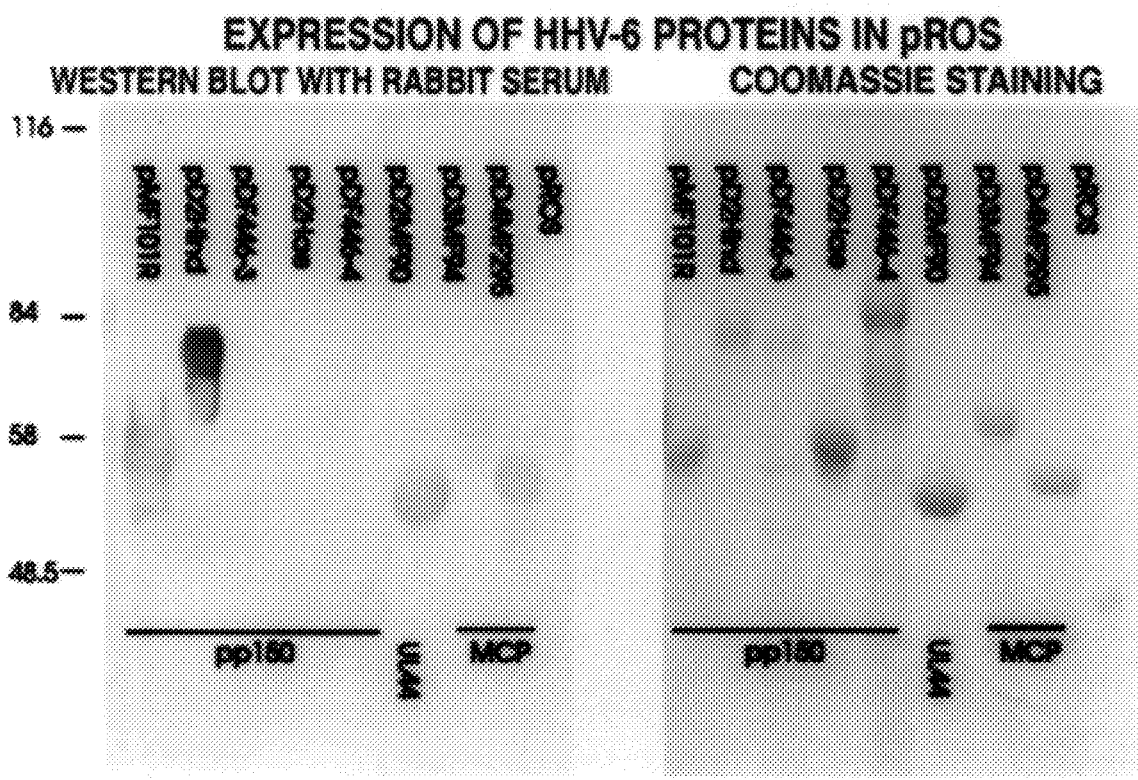
FIG. 6 shows the results of the expression of HHV-6 proteins in the expression vector pROS in a Western blot with rabbit serum and a PAGE Coomassie staining.
Figure 7:
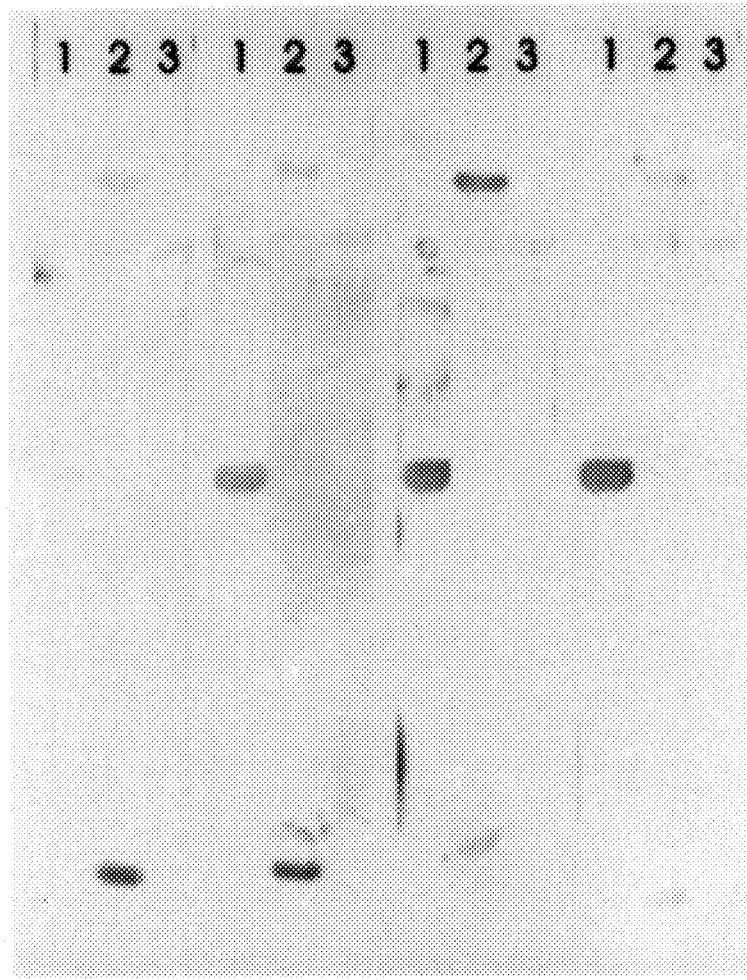
FIG. 7 shows the reactivity of the serum of four patients with HHV-6 epitopes.

Five fragments of p100, comprising almost the complete protein (pDF446-4, (SEQ ID NO:9) pDF446-3, (SEQ ID NO:10) pD2Hae, (SEQ ID NO:11) pD2Hind, (SEQ ID NO:12) pMF101R), (SEQ ID NO:13) were prokaryotically expressed as β-galactosidase fusion protein in the vector pROS (Ellinger et al). In Western blot assays only the carboxyterminal clones reacted with both rabbit human HHV-6 positive sera (FIG. 6, FIG. 7). Fusion protein expressed from pMF101R (SEQ ID NO:13) was used to purify antibodies from rabbit serum as described above. The antibodies were used to carry out Western blot analyses with HHV-6 infected and uninfected HSB-2 cells. A protein of 100 kda was detected in infected cells only. Of all expression clones investigated so far the carboxyterminal parts of p100 were most reliably recognized by human HHV-6 positive sera in Western blot analyses. Since it would be possible only with great technical elaboration to isolate virion proteins in the amounts necessary for diagnostic aids, the manner of preparation by gene manipulation according to the invention is especially advantageous. In Western blot analyses using HHV-6 infected cells a protein of 100 da is recognized most reliably by human sera. It could not have been expected that prokaryotically expressed p100 or parts thereof are invariably recognized by human sera, as the homologous gene of HCMV codes for a much larger protein, and the immunogenic parts of the HHV-6 gene did not show any homology to HCMV pp150. It is also surprising that the prokaryotically expressed part of an phosphorylated HHV-6 protein homologous to HCMV UL44 (pMF90) (SEQ ID NO:7) is recognized by most HHV-6 positive human sera.

It is possible according to the invention to use p100 and/or the fragment of the UL44 homologue of HHV-6 (pMF90) (SEQ ID NO:7) and/or the phosphorylated HHV-6 protein of 41 kD, or immunogenic parts thereof, which have been prepared in prokaryotic or eukaryotic cells, for example yeast cells, human or animal cells, as a reagent for detecting HHV-6 antibodies, for example in an ELISA assay.

EXAMPLE

A fragment of 182 bp from the carboxyterminal part of HHV-6 p100 (nucleotides 2960–3141 in FIG. 3) was ligated in the expression vector pROS (Ellinger, S. et al., 1989). The clone is termed pMF101R. The BamHI-HindIII fragments from plasmid pMF90, (SEQ ID NO:13) pMF94, and pMF295 were also ligated into pROS. They are termed pD2MF90, (SEQ ID NO:7) pD2MF94, (SEQ ID NO:5) and pD2MF295, (SEQ ID NO:6) respectively. Transformation of the resulting hybrid plasmid into *E. coli* JK50 was followed by isolation of clones whose plasmid DNA had the expected restriction pattern. After induction of the lac promoter with isopropyl-β-D-thiogalactopyranoside (IPTG) the clones expressed large amounts of a fusion protein having a viral fraction. The fusion proteins were isolated from the bacterial cells and used in Western blotting experiments. All human sera that were HHV-6 positive in a standard immunofluorescence assay using HHV-6 infected HSB-2 cells recognized at least one of the fusion proteins (FIG. 6). Human sera that were found to be HHV-6 negative using the immunofluorescence did react weakly or not at all.

Thus, prokaryotically expressed parts of p100 or the UL44 homologue of HHV-6 can be used in a diagnostic assay that is more sensitive and specific than the immunofluorescence used so far.

References

Chang, C. K. and Balachandran, N. (1991) Identification, Characterization, and Sequence Analysis of a cDNA Encoding a Phosphoprotein of Human Herpesvirus 6. J. Virol., 65:2884–2894.

Larcher, C., Huemer, H. P., Margreiter, R., and Dierich, M. P. (1988) Serological crossreaction of human herpesvirus-6 with cytomegalovirus [letter]. Lancet, 2:963–964.

Lawrence, G. L., Chee, M., Craxton, M. A., Gompels, U. A., Honess, R. W., and Barrell, B. G. (1990) Human herpesvirus 6 is closely related to human cytomegalovirus. J. Virol., 64:287–299.

Littler, E., Lawrence, G., Liu, M. Y., Barrell, B. G., and Arrand, J. R. (1990) Identification, cloning, and expression of the major capsid protein gene of human herpesvirus 6. J. Virol., 64:714–722.

Neipel, F., Ellinger, K., and Fleckenstein, B. (1991) The unique region of the human herpesvirus type 6 genome is essentially colinear to the UL segment of human cytomegalovirus. J. Gen. Virol., Yamamoto, M., Black, J. B., Stewart, J. A., Lopez, C., and Pellett, P. E. (1990) Identification of a nucleocapsid protein as a specific serological marker of human herpesvirus 6 infection. J. Clin. Microbiol., 28:1957–1962.

---

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 870 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Asp Leu Gln Arg His Pro Ile Pro Phe Ala Trp Leu Asp Arg Asp
 1               5                  10                  15

Lys Val Glu Arg Leu Thr Asp Phe Leu Ser Asn Leu Glu Arg Leu Asp
                20                  25                  30

Asn Val Asp Leu Arg Glu His Pro His Val Thr Asn Ser Cys Val Val
            35                  40                  45

Arg Glu Gly Asp Asp Val Asp Asp Leu Lys Thr Leu Tyr Asn Leu Leu
        50                  55                  60

Val Leu Trp Leu Met Tyr His Tyr Val Leu Ser Lys Arg Lys Pro Asp
65                  70                  75                  80

Tyr Asn Ala Ile Trp Gln Asp Ile Thr Lys Leu Gln Ser Val Val Asn
                85                  90                  95

Glu Tyr Leu Asn Ser Lys Gly Leu Asn Lys Gly Ile Phe Glu Asn Met
               100                 105                 110
```

```
Phe Thr Asn Lys Glu Lys Phe Glu Ser Gln Phe Ser Asp Ile Asn Arg
            115             120                 125
Ala Leu Leu Arg Leu Gly Asn Phe Ile Lys Trp Gly Ser Asn Val Ala
            130             135             140
Ile Asp Thr Pro Tyr Val Asn Leu Thr Ala Glu Asp Ser Ser Glu Ile
145             150             155                         160
Glu Asn Asn Leu Gln Asp Ala Glu Lys Asn Met Leu Trp Tyr Thr Val
            165             170                     175
Tyr Asn Ile Asn Asp Pro Trp Asp Glu Asn Gly Tyr Leu Ile Thr Ser
            180             185             190
Ile Asn Lys Leu Ile Tyr Leu Gly Lys Leu Phe Leu Ala Leu Thr Gln
            195             200             205
Ser Trp Ser Lys Leu Glu Lys Val Ala Met Ser Gln Ile Val Ile Thr
    210             215             220
Gln Asn His Leu Ser Gly His Leu Arg Arg His Asp Asn Phe Asn Ile
225             230             235                         240
Val Tyr Ser His Arg Val Leu Gln Thr Pro Leu Thr Gly Gln Arg Val
            245             250             255
Glu Ser Phe Leu Lys Ile Ile Thr Ser Asp Tyr Asp Ile Ile Lys Ser
            260             265             270
Ser Leu Glu Ser His Ser Ala Ser Lys Ala Phe Ser Met Ser Glu Ile
        275             280             285
Gly Pro Asn Ser Leu Met Asp Phe Val Pro Leu Arg Gly Asp Ile His
        290             295             300
Ser Asn Leu Thr Leu Pro Ser Met Ser Ile Asp Thr Lys Lys Ser Ser
305             310             315                         320
Leu Asp Pro Ala Arg Leu Lys Lys Ser Asn Ser Arg Ser Leu Asp Ser
            325             330             335
Phe Leu Arg Met Gln Arg Gln Pro Lys Phe Leu Glu Leu Asp Ser Val
            340             345             350
Asp Asn Ala Gly Glu Lys Ile Leu Leu Lys Glu Ala Thr Leu Gly Gly
            355             360             365
Glu Asn Val Lys Ala Thr Thr Pro Ala Ser Ser Val Ser Leu Met Ser
    370             375             380
Gly Val Glu Ser Pro Ser Phe Thr Ser Thr Asn Leu Asp Leu Pro Pro
385             390             395                         400
Leu Ser Ser Phe Thr Ser Thr Asn Leu Asp Leu Arg Asp Lys Ser His
            405             410             415
Gly Asn Tyr Lys Ile Gly Pro Ser Gly Ile Leu Asp Phe Asn Val Lys
            420             425             430
Phe Pro Pro Asn Ala Gln Leu Asn Thr Asn Gly Val Asp Leu Leu Gln
            435             440             445
Asp Lys Thr Ser Ile Gly Ser Pro Ser Ser Gly Ile Thr Asp Val Val
    450             455             460
Asn Gly Phe Ala Asn Leu Asn Leu His Gln Asn Lys Ser Asn Val Ser
465             470             475                         480
Pro Pro Trp Ser Arg Asn Thr Ala Ala Asn Ala Asp Phe Leu Asp Pro
            485             490             495
Val His Arg Phe Val Pro Glu Gln Thr Gly Thr Pro Phe Val Leu Asn
            500             505             510
Asn Ser Asp Val Ala Gly Ser Glu Ala Lys His Thr Thr Tyr Ser Thr
        515             520             525
Glu Thr Gly Val Ser Pro Arg Asn Val Phe Leu Ile Lys Asp Leu Arg
```

```
                              530                          535                          540

Gly   Lys   Asp   Gly   Phe   Arg   Lys   Gln   Lys   Gln   Ser   Asp   Ile   Pro   Lys   Ser
           545                           550                           555                           560

Leu   Thr   Lys   Glu   Arg   Asn   Asp   Lys   Ala   Ile   Met   His   Ser   Arg   Glu   Val
                                   565                           570                           575

Thr   Gly   Asp   Ser   Gly   Asp   Ala   Thr   Glu   Thr   Val   Gly   Ala   Arg   Asn   Ser
                             580                           585                           590

Pro   Ala   Leu   Arg   Lys   Ile   Lys   Gln   Ala   Asn   Asp   Phe   Phe   Ala   Gly   Leu
                             595                           600                           605

Asn   Lys   Lys   Asn   Asp   Arg   Asp   Val   Leu   Arg   Gly   Gly   Lys   Gly   Asn   Ser
                       610                           615                           620

Lys   Asp   Leu   His   Ser   Gly   Gly   Asn   Ala   Lys   Lys   Lys   Glu   Met   Ser   Gly
           625                           630                           635                           640

Lys   Phe   Asn   Asp   Asp   Lys   Glu   Met   Thr   Arg   Asn   Gly   Gln   Glu   Pro   Ser
                                   645                           650                           655

Arg   Ser   Leu   Met   Gly   Asp   Ala   Arg   Asn   Ala   Gly   Asp   Glu   Gln   Tyr   Ile
                                   660                           665                           670

Gln   Ala   Gly   Leu   Gly   Gln   Arg   Val   Asn   Asn   Leu   Leu   Ser   Gln   Phe   Thr
                             675                           680                           685

Asn   Leu   Ile   Ser   Leu   Gly   Glu   Lys   Gly   Ile   Glu   Asp   Ile   Leu   Gln   Asn
                       690                           695                           700

Gln   Arg   Gly   Thr   Glu   Leu   Lys   Leu   Ala   Thr   Glu   Asn   Lys   Ser   Gly   Arg
           705                           710                           715                           720

Glu   Ser   Glu   Glu   Ala   Asn   Val   Glu   Lys   Ile   Leu   Glu   Val   Ser   Asn   Pro
                                   725                           730                           735

Gln   Asp   Met   Phe   Lys   Asn   Phe   Arg   Leu   Gln   Asn   Asp   Leu   Asp   Ser   Val
                             740                           745                           750

Gln   Ser   Pro   Phe   Arg   Leu   Pro   Asp   Ala   Asp   Leu   Ser   Arg   Glu   Leu   Asp
                       755                           760                           765

Ser   Ala   Ser   Phe   Lys   Asp   Ala   Leu   Asp   Leu   Lys   Leu   Pro   Gly   Asn   Gly
                       770                           775                           780

Glu   Arg   Glu   Ile   Asp   Leu   Ala   Leu   Glu   Lys   Val   Lys   Val   Gly   Glu   Thr
           785                           790                           795                           800

Glu   Thr   Ser   Asp   Leu   Lys   Val   Gly   Gln   Asp   Glu   Ser   Phe   Val   Pro   Ala
                                   805                           810                           815

Gln   Leu   Met   Lys   Val   Glu   Thr   Pro   Glu   Glu   Lys   Asp   Asp   Ile   Ile   Glu
                             820                           825                           830

Gln   Met   Val   Leu   Arg   Ile   Arg   Gln   Asp   Gly   Glu   Thr   Asp   Glu   Asn   Thr
                             835                           840                           845

Val   Ser   Gly   Pro   Gly   Val   Ala   Glu   Ser   Leu   Asp   Ile   Glu   Ala   Lys   Gly
                       850                           855                           860

Glu   Ser   Ala   Ile   Ala   Ser
           865                           870
```

(2) INFORMATION FOR SEQ ID NO:2:

(i) SEQUENCE CHARACTERISTICS:
        (A) LENGTH: 2610 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
ATGGATCTGC  AAAGACATCC  GATTCCGTTT  GCGTGGCTAG  ATCGAGACAA  AGTTGAGCGT          60
```

| | | | | | |
|---|---|---|---|---|---|
| CTTACAGATT | TTCTCAGCAA | TTTGGAAAGA | CTGGATAATG | TAGATTTGCG | AGAGCATCCC | 120
| CATGTGACTA | ATTCTTGTGT | CGTGAGAGAG | GGAGACGATG | TAGACGATTT | AAAAACATTG | 180
| TATAACCTAC | TAGTGTTATG | GCTTATGTAT | CACTACGTCT | TATCTAAAAG | GAAGCCGGAT | 240
| TATAATGCTA | TATGGCAAGA | CATCACGAAA | CTCCAAAGTG | TCGTAAACGA | GTACTTAAAC | 300
| TCCAAAGGTC | TGAATAAAGG | AATTTTTGAA | AATATGTTCA | CGAACAAAGA | AAAGTTTGAA | 360
| TCGCAATTCA | GTGATATTAA | TCGCGCTTTA | CTGCGTTTAG | GAAACTTTAT | TAAGTGGGGT | 420
| AGCAATGTTG | CGATCGATAC | TCCTTATGTA | AATCTTACTG | CAGAAGACAG | CAGCGAGATA | 480
| GAAAATAATT | TGCAAGATGC | TGAAAAAAAC | ATGCTGTGGT | ATACCGTCTA | TAACATAAAT | 540
| GACCCCTGGG | ACGAAAACGG | TTACTTAATA | ACGAGTATTA | ATAAATTAAT | TTATCTCGGT | 600
| AAGTTATTTT | TAGCGTTAAC | TCAGTCCTGG | TCAAAGCTAG | AAAAGGTTGC | TATGAGTCAA | 660
| ATTGTAATCA | CGCAAAATCA | TCTCTCGGGT | CATTTGAGGA | GGCACGACAA | TTTTAATATT | 720
| GTATATTCTC | ATAGGGTTTT | GCAGACTCCT | CTGACTGGTC | AAAGAGTAGA | GAGTTTTCTG | 780
| AAAATAATCA | CCAGTGATTA | TGATATTATC | AAAAGTAGTC | TGGAATCACA | CAGCGCGTCG | 840
| AAAGCATTTT | CGATGTCTGA | GATTGGGCCT | AATTCTTTAA | TGGATTTCGT | CCCTTTACGC | 900
| GGCGATATAC | ATTCAAATTT | GACTTTACCT | AGTATGTCTA | TAGATACAAA | GAAATCATCT | 960
| TTAGATCCGG | CTCGTCTGAA | AAAAAGTAAT | TCCAGAAGTT | TGGATAGTTT | CTTAAGAATG | 1020
| CAGAGACAAC | CTAAATTTCT | AGAGTTGGAT | AGCGTTGATA | ATGCCGGGGA | AAAAATTTTA | 1080
| CTAAAGGAAG | CAACACTCGG | GGGTGAAAAC | GTTAAAGCGA | CAACGCCTGC | TTCCTCTGTC | 1140
| TCTTTAATGT | CCGGAGTTGA | GTCGCCGTCG | TCTTTCACTT | CTACCAATCT | GGATCTGCCG | 1200
| TTGTCGTCTT | TCACTTCTAC | TAATCTGGAT | CTGCGAGATA | AGTCGCACGG | TAATTATAAA | 1260
| ATTGGCCCTT | CGGGGATTTT | AGATTTTAAT | GTTAAATTTC | CACCTAATGC | GCAATTGAAT | 1320
| ACGAACGGTG | TGGATTTACT | ACAGGATAAA | ACTTCGATCG | GGAGTCCCAG | TAGCGGTATT | 1380
| ACCGATGTGG | TAAATGGTTT | CGCTAATCTC | AATCTGCATC | AGAATAAATC | AAATGTTTCG | 1440
| CCACCGTGGA | GCAGAAACAC | AGCGGCGAAT | GCGGACTTTT | TAGATCCGGT | GCATCGCTTT | 1500
| GTTCCTGAGC | AGACAGGGAC | ACCCTTCGTG | TTGAATAATT | CCGACGTGGC | GGGATCAGAA | 1560
| GCGAAGCATA | CGACTTACAG | TACGGAGACC | GGCGTTTCAC | CCCGTAACGT | TTTTCTCATT | 1620
| AAAGATTTGA | GAGGCAAAGA | CGGTTTTAGG | AAACAGAAGC | AGTCAGATAT | TCCGAAAAGC | 1680
| TTAACTAAGG | AAAGAAATGA | TAAAGCTATA | ATGCACTCAC | GCGAGGTGAC | CGGAGATTCT | 1740
| GGCGATGCGA | CTGAAACTGT | GGGTGCTCGG | AATTCCCCGG | CGTTGAGAAA | AATTAAGCAA | 1800
| GCAAATGATT | TTTTTGCCGG | GTTAAATAAG | AAAAATGATC | GTGACGTATT | AAGAGGGGGG | 1860
| AAAGGAAATA | GCAAGGACTT | GCATTCTGGC | GGCAATGCAA | AAAAAAAGA | AATGTCGGGA | 1920
| AAGTTTAATG | ACGATAAAGA | AATGACGCGA | AACGGACAAG | AGCCATCACG | TAGTTTAATG | 1980
| GGAGATGCTA | GAAATGCCGG | AGATGAACAA | TATATTCAAG | CGGGTCTCGG | GCAGCGAGTT | 2040
| AACAATCTTC | TAAGTCAATT | TACAAATCTG | ATTAGTTTAG | GCGAGAAGGG | CATCGAAGAC | 2100
| ATTTTGCAGA | ATCAGCGCGG | GACCGAGTTA | AAGTTGGCTA | CAGAAAACAA | GTCGGGACGC | 2160
| GAATCGGAGG | AAGCTAACGT | AGAAAAAATT | CTTGAAGTTA | GTAATCCTCA | AGATATGTTT | 2220
| AAAAATTTTA | GGTTGCAAAA | CGATCTCGAT | TCCGTTCAGT | CTCCGTTTAG | GCTACCGGAT | 2280
| GCTGATTTGT | CTCGCGAGTT | AGATTCCGCG | TCATTTAAGG | ACGCGTTAGA | CTTGAAGCTT | 2340
| CCGGGTAACG | GAGAACGAGA | AATAGATCTC | GCTCTTGAAA | AAGTGAAGGT | AGGCGAGACG | 2400
| GAAACCTCAG | ATTTAAAAGT | CGGTCAGGAT | GAAAGTTTTG | TTCCTGCGCA | ATTAATGAAG | 2460

| | | | | | |
|---|---|---|---|---|---|
| GTTGAGACAC | CTGAAGAAAA | AGATGATATA | ATTGAACAGA | TGGTTCTGAG | GATACGTCAA | 2520 |
| GACGGGGAAA | CTGATGAAAA | CACCGTCTCT | GGGCCGGGAG | TCGCTGAGTC | TTTGGATATA | 2580 |
| GAAGCCAAAG | GCGAGTCAGC | GATCGCGTCG | | | | 2610 |

( 2 ) INFORMATION FOR SEQ ID NO:3:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Ala  Leu  Asp  Leu  Lys  Leu  Pro  Gly  Asn  Gly  Glu  Arg  Glu  Ile  Asp  Leu
 1              5                        10                             15
Ala  Leu  Glu  Lys  Val  Lys  Val  Gly  Glu  Thr  Glu  Thr  Ser  Asp  Leu  Lys
            20                       25                       30
Val  Gly  Gln  Asp  Glu  Ser  Phe  Val  Pro  Ala  Gln  Leu  Met  Lys  Val  Glu
        35                       40                       45
Thr  Pro  Glu  Glu  Lys  Asp  Asp  Ile  Ile  Glu  Gln  Met  Val
      50                       55                       60
```

( 2 ) INFORMATION FOR SEQ ID NO:4:

( i ) SEQUENCE CHARACTERISTICS:
        ( A ) LENGTH: 552 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| GAATTCCCCG | GCGTTGAGAA | AAATTAAGCA | AGCAAATGAT | TTTTTTGCCG | GGTTAAATAA | 60 |
| GAAAAATGAT | CGTGACGTAT | TAAGAGGGGG | GAAAGGAAAT | AGCAAGGACT | TGCATTCTGG | 120 |
| CGGCAATGCA | AAAAAAAAAG | AAATGTCGGG | AAAGTTTAAT | GACGATAAAG | AAATGACGCG | 180 |
| AAACGGACAA | GAGCCATCAC | GTAGTTTAAT | GGGAGATGCT | AGAAATGCCG | GAGATGAACA | 240 |
| ATATATTCAA | GCGGGTCTCG | GGCAGCGAGT | TAACAATCTT | CTAAGTCAAT | TTACAAATCT | 300 |
| GATTAGTTTA | GGCGAGAAGG | GCATCGAAGA | CATTTTGCAG | AATCAGCGCG | GGACCGAGTT | 360 |
| AAAGTTGGCT | ACAGAAAACA | AGTCGGGACG | CGAATCGGAG | GAAGCTAACG | TAGAAAAAAT | 420 |
| TCTTGAAGTT | AGTAATCCTC | AAGATATGTT | TAAAAATTTT | AGGTTGCAAA | ACGATCTCGA | 480 |
| TTCCGTTCAG | TCTCCGTTTA | GGCTACCGGA | TGCTGATTTG | TCTCGCGAGT | TAGATTCCGC | 540 |
| GTCATTTAAG | GA | | | | | 552 |

( 2 ) INFORMATION FOR SEQ ID NO:5:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| GAATTCCTGA | CGCCAGCGCC | ACAGGCCTTG | TTATTTGATA | GTGCCGGGAG | TACGCAGAAG | 60 |
| TAAAATATCT | TGCTCAGGAT | GGTGGTTTCG | TTCGATGGTC | TGTCATTGTC | GGTAAAGACG | 120 |

| | | | | | | |
|---|---|---|---|---|---|---|
| ACGCTTGAAT | CTATTAGATT | CATTCTTTGC | ACATCGGATA | TTTCGTAATT | TCTAACTCTT | 180 |
| ACGGTGTTCT | GTGTCAGTGG | TGTATCATCC | GCTGTTATTT | TTGCATTCGT | GTCGTTTCTG | 240 |
| GGCATGGTAT | GGACGAACGG | GCAGAACAGA | CGTCCGTCGA | ACAACGCGTT | GGCGAAATTC | 300 |
| ACCAGAGGTT | CGCCGCAAAG | TTGCTCGTTG | AGGTTGGAGA | TAGAGATTGT | TCTCTTCACT | 360 |
| AGGCGAATTA | GCGACACAAG | ATTTCTGTAG | TGAGCGAAAG | CTGCTCCCGG | GATCAGTTCG | 420 |
| TCGCCCATGT | GGTTGGAATT | C | | | | 441 |

( 2 ) INFORMATION FOR SEQ ID NO:6:

( i ) SEQUENCE CHARACTERISTICS:
        ( A ) LENGTH: 219 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
| CCGTGTGAAA | TTAAACGACA | CCATGGAAAA | CAACCTACCC | ACCAGCGTTT | TTTTCCACAA | 60 |
| TAAAGACCAA | GTCGTGCAGC | GAATTGATTT | TGCCGACATA | TTACCGTCGG | TTTGCCATCC | 120 |
| CATTGTCCAC | GACTCGACCA | TCGTCGAACG | ACTCATGAAA | AGCGAACCAT | TGCCTACCGG | 180 |
| CCACCGCTTT | TCCCAACTAT | GTCAACTAAA | AATTACCCG | | | 219 |

( 2 ) INFORMATION FOR SEQ ID NO:7:

( i ) SEQUENCE CHARACTERISTICS:
        ( A ) LENGTH: 205 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | | |
|---|---|---|---|---|---|---|
| CCACTTTTTG | AAAGTTTTAT | GAACATCATC | TCGAATCCTG | AGGTTACGAA | GATGTACATT | 60 |
| CAGCATGATA | GTGATCTGTA | TACGAGGGTT | TTGGTAACGG | CTTCCGATAC | ATGTACACAG | 120 |
| GCGTCGGTTC | CCTGTGTGCA | CGGACAAGAA | GTGGTGCGAG | ACACCGGGAG | ATCGCCGTTG | 180 |
| AGGATTGACC | TTGATCATTC | GACCG | | | | 205 |

( 2 ) INFORMATION FOR SEQ ID NO:8:

( i ) SEQUENCE CHARACTERISTICS:
        ( A ) LENGTH: 3868 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base
        ( B ) LOCATION: 14
        ( D ) OTHER INFORMATION: /mod_base=OTHER
            / note= "N is unknown."

( i x ) FEATURE:
        ( A ) NAME/KEY: modified_base
        ( B ) LOCATION: 3695
        ( D ) OTHER INFORMATION: /mod_base=OTHER
            / note= "N is unknown."

( x i ) SEQUENCE DESCRIPTION: SEQ ID NO:8:

| | | | | | | |
|---|---|---|---|---|---|---|
| GAATTCCTAT | GTTNCGCCCC | GTGCTAGATG | TTTTACTTTC | AGTCTTTTTA | CGCCGGTGTA | 60 |

| | | | | | |
|---|---|---|---|---|---|
| AGGTTTTGTA | CCTGATAGTT | GCGATTATAG | CTAGCATGCT | TATACTATAT | GAACAGACTG | 120 |
| CATGATAGAT | GAAGTAAACT | AACTGACAGA | AAAAACGGTT | GAATGAGAAC | AGTTGCTTTC | 180 |
| TGTTCACTGT | CATAAAAAAG | ACACACCACA | TGAGCACAAA | ATCGCTAGCA | AAGAGTGTGA | 240 |
| TGACGTAAAA | TGAAGTAGCG | TTATGTTTTG | CGACTCTGTG | GTAGAGAATC | ATGGTGGTAA | 300 |
| CCACTATAAT | GATCATGGGG | ATAGATGTGG | TGAGCGTGAT | TCCGGTAACT | GCGCTCTCCA | 360 |
| TGATTCGTGC | TGTCTTTAGC | GTGGGTGTCG | AGGTACAGGA | AGCATTGCCT | TTGAACTCTT | 420 |
| CATTGCGCTA | TTAAAGATAT | TGAATGTTAT | TTTCATGTTA | CGCTACATTA | AAATATTCGG | 480 |
| TAACAATGAT | GTCTGAAGAC | TTACCAGAAG | TTTGGACAGC | TCAATGACAG | TGTCCATCTC | 540 |
| GTCGCTTGTC | AGTTTTCTGT | GTGGGTAAAA | AAAAGACTAT | TAAACATTGA | ATGTTGGCGG | 600 |
| AAATGAGCAG | TTCTGTTTTT | GAGTTTGTTT | TCTAAAATAT | GGATCTGCAA | AGACATCCGA | 660 |
| TTCCGTTTGC | GTGGCTAGAT | CGAGACAAAG | TTGAGCGTCT | TACAGATTTT | CTCAGCAATT | 720 |
| TGGAAAGACT | GGATAATGTA | GATTGCGAG | AGCATCCCCA | TGTGACTAAT | TCTTGTGTCG | 780 |
| TGAGAGAGGG | AGACGATGTA | GACGATTTAA | AAACATTGTA | TAACCTACTA | GTGTTATGGC | 840 |
| TTATGTATCA | CTACGTCTTA | TCTAAAAGGA | AGCCGGATTA | TAATGCTATA | TGGCAAGACA | 900 |
| TCACGAAACT | CCAAAGTGTC | GTAAACGAGT | ACTTAAACTC | CAAAGGTCTG | AATAAAGGAA | 960 |
| TTTTTGAAAA | TATGTTCACG | AACAAAGAAA | AGTTTGAATC | GCAATTCAGT | GATATTAATC | 1020 |
| GCGCTTTACT | GCGTTTAGGA | AACTTTATTA | AGTGGGGTAG | CAATGTTGCG | ATCGATACTC | 1080 |
| CTTATGTAAA | TCTTACTGCA | GAAGACAGCA | GCGAGATAGA | AAATAATTTG | CAAGATGCTG | 1140 |
| AAAAAAACAT | GCTGTGGTAT | ACCGTCTATA | ACATAAATGA | CCCCTGGGAC | GAAAACGGTT | 1200 |
| ACTTAATAAC | GAGTATTAAT | AAATTAATTT | ATCTCGGTAA | GTTATTTTA | GCGTTAACTC | 1260 |
| AGTCCTGGTC | AAAGCTAGAA | AAGGTTGCTA | TGAGTCAAAT | TGTAATCACG | CAAAATCATC | 1320 |
| TCTCGGGTCA | TTTGAGGAGG | CACGACAATT | TTAATATTGT | ATATTCTCAT | AGGGTTTTGC | 1380 |
| AGACTCCTCT | GACTGGTCAA | AGAGTAGAGA | GTTTTCTGAA | AATAATCACC | AGTGATTATG | 1440 |
| ATATTATCAA | AAGTAGTCTG | GAATCACACA | GCGCGTCGAA | AGCATTTTCG | ATGTCTGAGA | 1500 |
| TTGGGCCTAA | TTCTTTAATG | GATTTCGTCC | CTTTACGCGG | CGATATACAT | TCAAATTTGA | 1560 |
| CTTTACCTAG | TATGTCTATA | GATACAAAGA | AATCATCTTT | AGATCCGGCT | CGTCTGAAAA | 1620 |
| AAAGTAATTC | CAGAAGTTTG | GATAGTTTCT | TAAGAATGCA | GAGACAACCT | AAATTTCTAG | 1680 |
| AGTTGGATAG | CGTTGATAAT | GCCGGGGAAA | AAATTTTACT | AAAGGAAGCA | ACACTCGGGG | 1740 |
| GTGAAAACGT | TAAAGCGACA | ACGCCTGCTT | CCTCTGTCTC | TTTAATGTCC | GGAGTTGAGT | 1800 |
| CGCCGTCGTC | TTTCACTTCT | ACCAATCTGG | ATCTGCCGTT | GTCGTCTTTC | ACTTCTACTA | 1860 |
| ATCTGGATCT | GCGAGATAAG | TCGCACGGTA | ATTATAAAAT | TGGCCCTTCG | GGGATTTTAG | 1920 |
| ATTTTAATGT | TAAATTTCCA | CCTAATGCGC | AATTGAATAC | GAACGGTGTG | GATTACTAC | 1980 |
| AGGATAAAAC | TTCGATCGGG | AGTCCCAGTA | GCGGTATTAC | CGATGTGGTA | AATGGTTTCG | 2040 |
| CTAATCTCAA | TCTGCATCAG | AATAAATCAA | ATGTTTCGCC | ACCGTGGAGC | AGAAACACAG | 2100 |
| CGGCGAATGC | GGACTTTTA | GATCCGGTGC | ATCGCTTTGT | TCCTGAGCAG | ACAGGGACAC | 2160 |
| CCTTCGTGTT | GAATAATTCC | GACGTGGCGG | GATCAGAAGC | GAAGCATACG | ACTTACAGTA | 2220 |
| CGGAGACCGG | CGTTTCACCC | CGTAACGTTT | TTCTCATTAA | AGATTTGAGA | GGCAAAGACG | 2280 |
| GTTTTAGGAA | ACAGAAGCAG | TCAGATATTC | CGAAAAGCTT | AACTAAGGAA | AGAAATGATA | 2340 |
| AAGCTATAAT | GCACTCACGC | GAGGTGACCG | GAGATTCTGG | CGATGCGACT | GAAACTGTGG | 2400 |
| GTGCTCGGAA | TTCCCCGGCG | TTGAGAAAAA | TTAAGCAAGC | AAATGATTTT | TTTGCCGGGT | 2460 |

```
TAAATAAGAA    AAATGATCGT    GACGTATTAA    GAGGGGGGAA    AGGAAATAGC    AAGGACTTGC     2520

ATTCTGGCGG    CAATGCAAAA    AAAAAGAAA     TGTCGGGAAA    GTTTAATGAC    GATAAAGAAA     2580

TGACGCGAAA    CGGACAAGAG    CCATCACGTA    GTTTAATGGG    AGATGCTAGA    AATGCCGGAG     2640

ATGAACAATA    TATTCAAGCG    GGTCTCGGGC    AGCGAGTTAA    CAATCTTCTA    AGTCAATTTA     2700

CAAATCTGAT    TAGTTTAGGC    GAGAAGGGCA    TCGAAGACAT    TTTGCAGAAT    CAGCGCGGGA     2760

CCGAGTTAAA    GTTGGCTACA    GAAAACAAGT    CGGGACGCGA    ATCGGAGGAA    GCTAACGTAG     2820

AAAAAATTCT    TGAAGTTAGT    AATCCTCAAG    ATATGTTTAA    AAATTTTAGG    TTGCAAAACG     2880

ATCTCGATTC    CGTTCAGTCT    CCGTTTAGGC    TACCGGATGC    TGATTTGTCT    CGCGAGTTAG     2940

ATTCCGCGTC    ATTTAAGGAC    GCGTTAGACT    TGAAGCTTCC    GGGTAACGGA    GAACGAGAAA     3000

TAGATCTCGC    TCTTGAAAAA    GTGAAGGTAG    GCGAGACGGA    AACCTCAGAT    TTAAAAGTCG     3060

GTCAGGATGA    AAGTTTTGTT    CCTGCGCAAT    TAATGAAGGT    TGAGACACCT    GAAGAAAAAG     3120

ATGATATAAT    TGAACAGATG    GTTCTGAGGA    TACGTCAAGA    CGGGGAAACT    GATGAAAACA     3180

CCGTCTCTGG    GCCGGGAGTC    GCTGAGTCTT    TGGATATAGA    AGCCAAAGGC    GAGTCAGCGA     3240

TCGCGTCGTG    ATGTAAAAAA    TTTTCTCTGG    GGAGTTTCAG    GTTGCCAATA    AAATGCCCAT     3300

TCTCAGACAG    CTTTGCGATT    ACGTCTTTTT    GTTCATTGTT    CTGGCTTGTC    ATTCTTTCTA     3360

CATAAAACAG    GGTCGCGATA    GGTGTGCTTT    GAGGCAGGAT    CAGATTTGGA    GAAAATGAAC     3420

GCAGCGTAAT    GTGCAAAGGT    GTTCCCGGGG    CCCACAGCAT    CACCTGGGTT    TCGAAGAATC     3480

CTTCGTTCTG    GTAGCCGGAT    ATGAGGATTT    GCTTGTCGGG    CTTTGTGAAA    TATCGGATAG     3540

GTAGAATTAC    TATGTGGCAT    CGGCTTGGAT    AGAAATGGAT    GTCATATGGT    GCGTGTACAA     3600

GTAGCTCGTA    ATAATTTGGG    TTGTGTTGCA    GTTGTATCGT    TGCGTTTAGT    ACGTCTCCTG     3660

TAAAATATAA    TTTCGGGTTA    CTGGAAAATA    ACAGNGGTTC    GGGCTCTTCG    ATTTGCGTTA     3720

CCACTTCAAA    CTGAACTATT    AAATATTTCG    GTAGATTTTC    CGTTGTTAGT    AAAGAAGGGA     3780

TTTGCTCGCA    GCATACAGTG    GCTAGTGTTC    CAAAAACTTT    TTCTTTGTTT    TTGACGAGAC     3840

CGAGATTTTC    AATGTTAATC    GAGAATTC                                                3868
```

( 2 ) INFORMATION FOR SEQ ID NO:9:

( i ) SEQUENCE CHARACTERISTICS:
        ( A ) LENGTH: 697 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
TAAAAACATT    GTATAACCTA    CTAGTGTTAT    GGCTTATGTA    TCACTACGTC    TTATCTAAAA      60

GGAAGCCGGA    TTATAATGCT    ATATGGCAAG    ACATCACGAA    ACTCCAAAGT    GTCGTAAACG     120

AGTACTTAAA    CTCCAAAGGT    CTGAATAAAG    GAATTTTTGA    AAATATGTTC    ACGAACAAAG     180

AAAAGTTTGA    ATCGCAATTC    AGTGATATTA    ATCGCGCTTT    ACTGCGTTTA    GGAAACTTTA     240

TTAAGTGGGG    TAGCAATGTT    GCGATCGATA    CTCCTTATGT    AAATCTTACT    GCAGAAGACA     300

GCAGCGAGAT    AGAAAATAAT    TTGCAAGATG    CTGAAAAAAA    CATGCTGTGG    TATACCGTCT     360

ATAACATAAA    TGACCCCTGG    GACGAAAACG    GTTACTTAAT    AACGAGTATT    AATAAATTAA     420

TTTATCTCGG    TAAGTTATTT    TTAGCGTTAA    CTCAGTCCTG    GTCAAAGCTA    GAAAAGGTTG     480

CTATGAGTCA    AATTGTAATC    ACGCAAAATC    ATCTCTCGGG    TCATTTGAGG    AGGCACGACA     540
```

| | | | | | |
|---|---|---|---|---|---|
| ATTTTAATAT | TGTATATTCT | CATAGGGTTT | TGCAGACTCC | TCTGACTGGT | CAAAGAGTAG | 600 |
| AGAGTTTTCT | GAAAATAATC | ACCAGTGATT | ATGATATTAT | CAAAAGTAGT | CTGGAATCAC | 660 |
| ACAGCGCGTC | GAAAGCATTT | TCGATGTCTG | AGATTGG | | | 697 |

( 2 ) INFORMATION FOR SEQ ID NO:10:

( i ) SEQUENCE CHARACTERISTICS:
        ( A ) LENGTH: 505 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| | | | | | |
|---|---|---|---|---|---|
| GCCCTTCGGG | GATTTTAGAT | TTTAATGTTA | AATTTCCACC | TAATGCGCAA | TTGAATACGA | 60 |
| ACGGTGTGGA | TTTACTACAG | GATAAAACTT | CGATCGGGAG | TCCCAGTAGC | GGTATTACCG | 120 |
| ATGTGGTAAA | TGGTTTCGCT | AATCTCAATC | TGCATCAGAA | TAAATCAAAT | GTTTCGCCAC | 180 |
| CGTGGAGCAG | AAACACAGCG | GCGAATGCGG | ACTTTTAGA | TCCGGTGCAT | CGCTTTGTTC | 240 |
| CTGAGCAGAC | AGGGACACCC | TTCGTGTTGA | ATAATTCCGA | CGTGGCGGGA | TCAGAAGCGA | 300 |
| AGCATACGAC | TTACAGTACG | GAGACCGGCG | TTTCACCCCG | TAACGTTTTT | CTCATTAAAG | 360 |
| ATTTGAGAGG | CAAAGACGGT | TTTAGGAAAC | AGAAGCAGTC | AGATATTCCG | AAAAGCTTAA | 420 |
| CTAAGGAAAG | AAATGATAAA | GCTATAATGC | ACTCACGCGA | GGTGACCGGA | GATTCTGGCG | 480 |
| ATGCGACTGA | AACTGTGGGT | GCTCG | | | | 505 |

( 2 ) INFORMATION FOR SEQ ID NO:11:

( i ) SEQUENCE CHARACTERISTICS:
        ( A ) LENGTH: 399 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| GCCTAATTCT | TTAATGGATT | TCGTCCCTTT | ACGCGGCGAT | ATACATTCAA | ATTTGACTTT | 60 |
| ACCTAGTATG | TCTATAGATA | CAAAGAAATC | ATCTTTAGAT | CCGGCTCGTC | TGAAAAAAG | 120 |
| TAATTCCAGA | AGTTTGGATA | GTTTCTTAAG | AATGCAGAGA | CAACCTAAAT | TTCTAGAGTT | 180 |
| GGATAGCGTT | GATAATGCCG | GGGAAAAAAT | TTACTAAAG | GAAGCAACAC | TCGGGGGTGA | 240 |
| AAACGTTAAA | GCGACAACGC | CTGCTTCCTC | TGTCTCTTTA | ATGTCCGGAG | TTGAGTCGCC | 300 |
| GTCGTCTTTC | ACTTCTACCA | ATCTGGATCT | GCCGTTGTCG | TCTTTCACTT | CTACTAATCT | 360 |
| GGATCTGCGA | GATAAGTCGC | ACGGTAATTA | TAAAATTGG | | | 399 |

( 2 ) INFORMATION FOR SEQ ID NO:12:

( i ) SEQUENCE CHARACTERISTICS:
        ( A ) LENGTH: 566 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| GAATTCCCCG | GCGTTGAGAA | AAATTAAGCA | AGCAAATGAT | TTTTTGCCG | GGTTAAATAA | 60 |
| GAAAAATGAT | CGTGACGTAT | TAAGAGGGGG | GAAAGGAAAT | AGCAAGGACT | TGCATTCTGG | 120 |

-continued

| | | | | | | |
|---|---|---|---|---|---|---|
| CGGCAATGCA | AAAAAAAAG | AAATGTCGGG | AAAGTTTAAT | GACGATAAAG | AAATGACGCG | 180 |
| AAACGGACAA | GAGCCATCAC | GTAGTTTAAT | GGGAGATGCT | AGAAATGCCG | GAGATGAACA | 240 |
| ATATATTCAA | GCGGGTCTCG | GGCAGCGAGT | TAACAATCTT | CTAAGTCAAT | TTACAAATCT | 300 |
| GATTAGTTTA | GGCGAGAAGG | GCATCGAAGA | CATTTTGCAG | AATCAGCGCG | GGACCGAGTT | 360 |
| AAAGTTGGCT | ACAGAAACA | AGTCGGGACG | CGAATCGGAG | GAAGCTAACG | TAGAAAAAT | 420 |
| TCTTGAAGTT | AGTAATCCTC | AAGATATGTT | TAAAAATTTT | AGGTTGCAAA | ACGATCTCGA | 480 |
| TTCCGTTCAG | TCTCCGTTTA | GGCTACCGGA | TGCTGATTTG | TCTCGCGAGT | TAGATTCCGC | 540 |
| GTCATTTAAG | GACGCGTTAG | ACTTGA | | | | 566 |

(2) INFORMATION FOR SEQ ID NO:13:

(i) SEQUENCE CHARACTERISTICS:
  (A) LENGTH: 182 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:13:

| | | | | | | |
|---|---|---|---|---|---|---|
| CGCGTTAGAC | TTGAAGCTTC | CGGGTAACGG | AGAACGAGAA | ATAGATCTCG | CTCTTGAAAA | 60 |
| AGTGAAGGTA | GGCGAGACGG | AAACCTCAGA | TTTAAAAGTC | GGTCAGGATG | AAAGTTTTGT | 120 |
| TCCTGCGCAA | TTAATGAAGG | TTGAGACACC | TGAAGAAAAA | GATGATATAA | TTGAACAGAT | 180 |
| GG | | | | | | 182 |

We claim:

1. An isolated and purified DNA molecule having a nucleotide sequence encoding a human herpesvirus type 6 (HHV-6) protein p100 having the amino acid sequence given in FIG. 3 (SEQ ID NO:1).

2. The DNA molecule according to claim 1 having the nucleotide sequence from position 639 to position 3248 (SEQ ID NO:2).

3. A DNA molecule that hybridizes to a DNA molecule according to claim 2 and that encodes an HHV-6 p100 protein, wherein said protein binds to an antibody that specifically binds to the HHV-6 p100 protein encoded by the DNA molecule of claim 2; and wherein said antibody does not bind to a component of human cytomegalovirus or other herpesviruses.

4. A recombinant vector containing the DNA molecule according to claims 2 or 3.

5. The recombinant vector according to claim 4 in which said DNA molecule is operatively linked to a transcriptional promoter.

6. An in vitro host cell comprising the vector according to claim 5.

7. The transformed host cell of claim 6 wherein said cell is a bacterium, a yeast cell, a plant cell, or an animal cell.

8. A process for the production of an HHV-6 p100 protein, comprising culturing the transformed host cell of claim 6 and recovering an HHV-6 p100 protein from the culture.

9. A transformed host cell according to claim 7 wherein the bacterium is of the genus Escherichia, the yeast cell is of the genus Saccharomyces, and the animal cell is a mammalian cell.

10. A composition comprising the DNA molecule of claim 2.

11. The DNA molecule according to claim 1 having the nucleotide sequence given in FIG. 3 from position 2960 to position 3141 of SEQ ID NO;2.

12. The DNA molecule according to claim 1 having the nucleotide sequence given in FIG. 3 from position 2408 to position 2959 (SEQ ID NO:4).

* * * * *